(12) United States Patent
Bayat

(10) Patent No.: US 6,830,451 B1
(45) Date of Patent: Dec. 14, 2004

(54) DEVICE FOR ILLUMINATING ORAL CAVITY

(76) Inventor: Parissa T. Bayat, 31 Pacific Grove, Irvine, CA (US) 92602

( * ) Notice: Subject to any disclaimer, the term of this patent is extended or adjusted under 35 U.S.C. 154(b) by 0 days.

(21) Appl. No.: 10/644,164

(22) Filed: Aug. 21, 2003

(51) Int. Cl.[7] .............................. A61C 1/00; A61C 5/00
(52) U.S. Cl. ......................................... 433/29; 433/140
(58) Field of Search ......................... 433/29, 140, 93; 362/109, 116, 158, 190, 191

(56) References Cited

U.S. PATENT DOCUMENTS

| | | | | |
|---|---|---|---|---|
| 1,122,086 A | * | 12/1914 | Dunlop | ...................... 600/238 |
| 2,545,851 A | * | 3/1951 | Kardos | ........................ 446/485 |
| 2,696,382 A | * | 12/1954 | Gelardin | ....................... 472/57 |
| 5,226,712 A | * | 7/1993 | Lucas | ......................... 362/103 |
| 5,429,120 A | * | 7/1995 | Lewitus | ..................... 600/191 |
| 5,434,761 A | * | 7/1995 | Lesnick et al. | ............. 362/189 |
| 6,332,776 B1 | * | 12/2001 | Martin et al. | ............... 433/140 |
| 2004/0043349 A1 | * | 3/2004 | Liao | ........................... 433/29 |
| 2004/0063060 A1 | * | 4/2004 | Meyers et al. | ................ 433/29 |

* cited by examiner

Primary Examiner—Todd E. Manahan
(74) Attorney, Agent, or Firm—Vladimir Khiterer

(57) ABSTRACT

This invention relates to a device for illuminating oral cavity. A bite block comprised of a flexible biocompatible sterilizable molded material encapsulates within the molded material a battery, a pressure-sensing switch and a light. When a dental patient applies pressure to the bite block placed between the teeth, the light illuminates the oral cavity.

8 Claims, 3 Drawing Sheets

DEVICE FOR ILLUMINATING ORAL CAVITY

FIELD OF THE INVENTION

This invention relates to a device for illuminating oral cavity, and more specifically, a bite block comprising a self contained light source.

BACKGROUND OF THE INVENTION

Illumination of a patient's oral cavity is necessary for dental examinations and procedures. Conventionally, the oral cavity is illuminated by a focused light located above a dental chair. Illumination takes place through patient's mouth. Dentists are positioned between the light and patient's mouth, which often blocks the light and creates shadow in the patient's mouth and requires readjustment of the light.

To alleviate this problem, light delivered via fiber optic strands incorporated into handheld dental instruments is used. Use of fiber optic strands is expensive and inconvenient because the instruments equipped with fiber optic strands are not comfortable to operate. Also, sterilization is more difficult and causes the fiber optic strands to deteriorate over time.

What is needed is a simple and inexpensive means of illuminating the oral cavity.

SUMMARY OF THE INVENTION

This invention overcomes the drawbacks in the prior art and provides a simple nd inexpensive means of illuminating the oral cavity. Specifically, the device for illuminating oral cavity according to this invention comprises a bite block comprised of a flexible biocompatible sterilizable molded material, for example, rubber or any other appropriate material known to persons knowledgeable in the relevant arts. The material must be biocompatible because the bite block comes into a contact with the inside of patients' mouth. It must also be sterilizable for the same reason. The bite block may be formed by a compression molding process, a transfer molding process, a casting process, an injection molding process, or similar process known to persons knowledgeable in the relevant arts.

A DC battery, a pressure-sensing switch and a LED light are encapsulated within the molded material that forms the bite block. The DC battery and pressure-sensing switch are fully encapsulated within the molded material, whereas the LED light is partially encapsulated within the molded material and has a partially exposed portion. A lens can be disposed on that partially exposed portion.

The pressure-sensing switch is placed in an "on" position when pressure is applied to the bite block by teeth of a patient biting on the bite block when it is placed between the teeth. The pressure-sensing switch remains in an "off" position when pressure is not applied to the bite block. The pressure-sensing switch is electrically coupled with the DC battery and LED light such that when the pressure-sensing switch is placed in the "on" position, the LED light is energized causing illumination of patient's oral cavity. LED light should be positioned towards the area within the oral cavity that needs to be illuminated.

Due to the relatively inexpensive nature of the device for illuminating oral cavity according to this invention, it can be disposable. To this end, it can be sterilized and placed into a sealed sterile package by way of the process known to persons knowledgeable in the relevant arts.

BRIEF DESCRIPTION OF THE DRAWINGS FIGURES

DETAILED DESCRIPTION OF THE PREFERRED EMBODIMENTS

Figure 1:
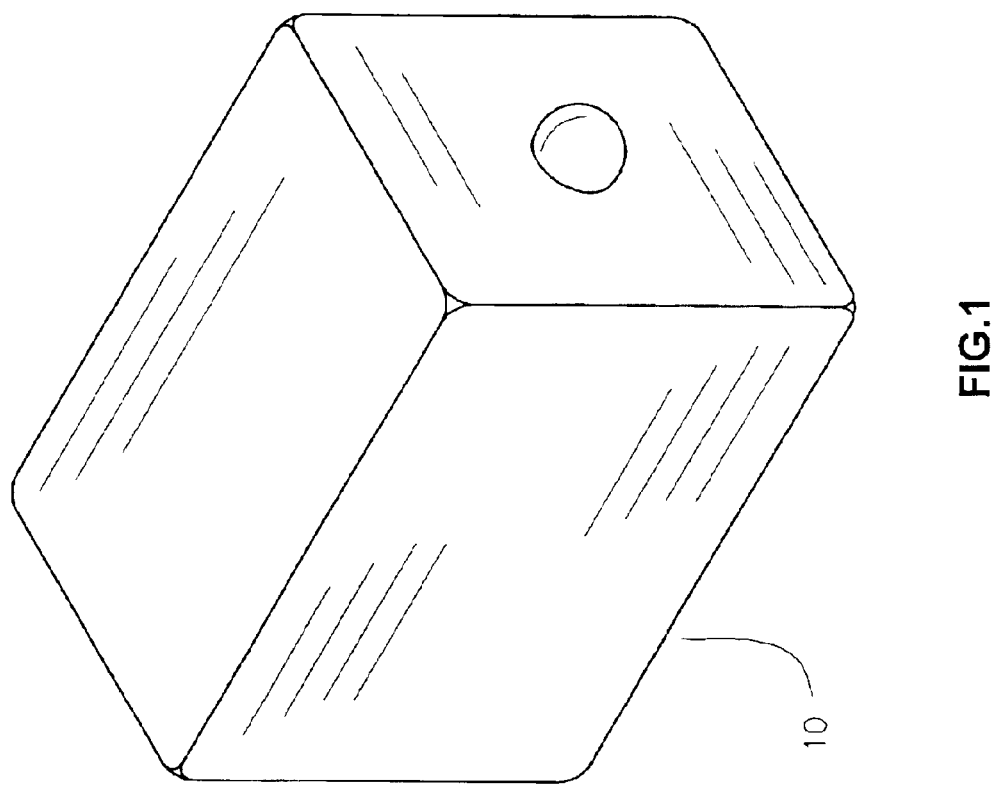
FIG. 1 shows an isometric view of the device according to the first embodiment of this invention.
Figure 2:
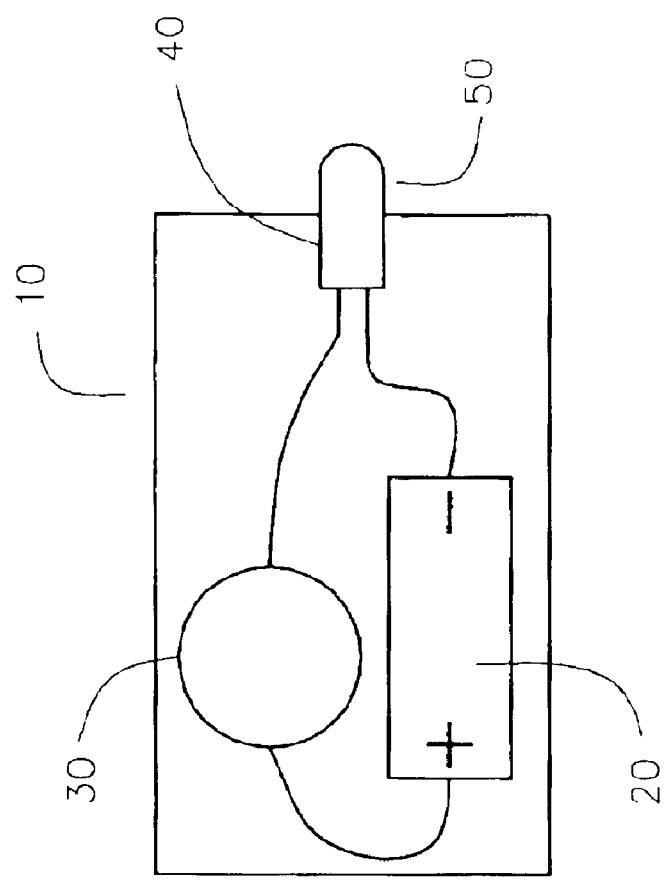
FIG. 2 shows a side cross sectional view of the device according to the first embodiment of this invention.
Figure 3:
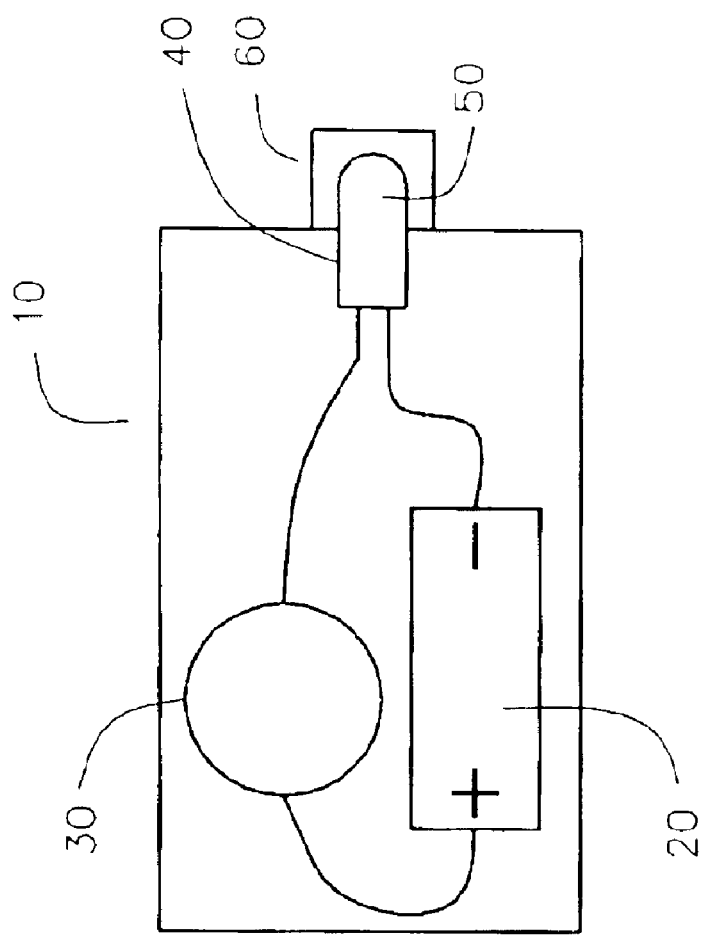
FIG. 3 shows a side cross sectional view of the device according to a second embodiment of this invention.

This invention will be better understood with the reference to the drawing figures FIG. 1 through FIG. 3. The same numerals indicate the same elements in all drawing figures. Viewing FIG. 1, there is shown a device for illuminating oral cavity according to this invention. Numeral 10 indicates a bite block. Bite Block 10 is comprised of a flexible biocompatible sterilizable molded material, for example, rubber or any other appropriate material known to persons knowledgeable in the relevant arts. The material must be biocompatible because the bite block comes into a contact with the inside of patients' mouth. It must also be sterilizable for the same reason. Bite Block 10 may be formed by a compression molding process, a transfer molding process, a casting process, an injection molding process, or similar process known to persons knowledgeable in the relevant arts.

Viewing now FIG. 2, numeral 20 indicates a battery means. Battery Means 20 is fully encapsulated within the molded material that forms Bite Block 10. Battery Means 20 is shown in FIG. 2 as a DC battery. However, it can be any battery known to persons knowledgeable in the relevant arts.

Numeral 30 indicates a pressure-sensing switch. Pressure-Sensing Switch 30 is fully encapsulated within the molded material that forms Bite Block 10. Numeral 40 indicates a light emitting means. Light Emitting Means 40 is partially encapsulated within the molded material that forms Bite Block 10 and has a partially exposed portion indicated by numeral 50. Light Emitting Means 40 is shown in FIG. 2 as a LED light. However, it can be any light known to persons knowledgeable in the relevant arts.

Pressure-Sensing Switch 30 is placed in an "on" position when pressure is applied to Bite Block 10 by teeth of a patient biting on Bite Block 10 when it is placed between the teeth. Specifically, due to the flexible nature of the molded material that forms Bite Block 10, pressure applied to Bite Block 10 by the teeth of the patient is transmitted to Pressure-Sensing Switch 30 and actuates the switch.

Pressure-Sensing Switch 30 remains in an "off" position when pressure is not applied to Bite Block 10. Pressure-Sensing Switch 30 is electrically coupled with Battery Means 20 and Light Emitting Means 40 such that when Pressure-Sensing Switch 30 is placed in the "on" position, Light Emitting Means 40 is energized causing illumination of patient's oral cavity. Light Emitting Means 40 should be positioned towards the area within the oral cavity that needs to be illuminated.

Viewing now FIG. 3, numeral 60 indicates a lens. Lens 60 is disposed on Partially Exposed Portion 50. Lens 60 is used to protect Light Emitting Means 40 and to focus the light for better illumination of the oral cavity.

While the present invention has been described and defined by reference to the preferred embodiment of the invention, such reference does not imply a limitation on the invention, and no such limitation is to be inferred. The invention is capable of considerable modification, alteration, and equivalents in form and function, as will occur to those ordinarily skilled and knowledgeable in the pertinent arts. The depicted and described preferred embodiments of the invention is exemplary only, and is not exhaustive of the scope of the invention. Consequently, the invention is intended to be limited only by the spirit and scope of the appended claims, giving full cognizance to equivalents in all respects.

What is claimed is:

1. A device for illuminating oral cavity comprising:
   (a) a bite block substantially rectangular comprised of a flexible biocompatible sterilizable molded material;
   (b) a battery means fully encapsulated within said molded material;
   (c) a pressure-sensing switch fully encapsulated within said molded material;
   (d) a light emitting means partially encapsulated within said molded material and having a partially exposed portion;
   wherein the pressure-sensing switch is placed in an "on" position when pressure is applied to the bite block by teeth of a patient biting on the bite block;
   wherein the pressure-sensing switch remains in an "off" position when pressure is not applied to the bite block;
   wherein the pressure-sensing switch is electrically coupled with the battery means and light emitting means such that when the pressure-sensing switch is placed in the "on" position, the light emitting means is energized causing illumination of patient's oral cavity.

2. A device for illuminating oral cavity as in claim 1, wherein the battery means is a DC battery.

3. A device for illuminating oral cavity as in claim 2, wherein the light emitting means is a LED light.

4. A device for illuminating oral cavity as in claim 3, wherein the bite block is further sterilized and placed into a sealed sterile package.

5. A device for illuminating oral cavity as in claim 1 further comprising a lens disposed on the partially exposed portion of the light emitting means.

6. A device for illuminating oral cavity as in claim 5, wherein the battery means is a DC battery.

7. A device for illuminating oral cavity as in claim 6, wherein the light emitting means is a LED light.

8. A device for illuminating oral cavity as in claim 7, wherein the bite block is further sterilized and placed into a sealed sterile package.

* * * * *